United States Patent [19]

Stöcker

[11] Patent Number: 4,647,543

[45] Date of Patent: Mar. 3, 1987

[54] PROCESS FOR ANALYSES TO BE CARRIED OUT ON IMMOBILIZED BIOLOGICAL TISSUE

[76] Inventor: Winfried Stöcker, Krummesserweg 3, D-2419 Rondeshagen, Fed. Rep. of Germany

[21] Appl. No.: 582,394

[22] Filed: Feb. 24, 1984

[30] Foreign Application Priority Data

Feb. 25, 1983 [EP] European Pat. Off. ........... 83101863

[51] Int. Cl.[4] .......................... G01N 1/28; G02B 21/34
[52] U.S. Cl. ........................................ 436/174; 424/3; 435/284
[58] Field of Search .......................... 424/3; 250/461.2; 350/536; 356/246; 436/172, 174, 503; 435/284, 808, 240

[56] References Cited

U.S. PATENT DOCUMENTS

| | | | |
|---|---|---|---|
| 2,965,219 | 12/1960 | Rhodin | 350/536 |
| 3,556,633 | 1/1971 | Mutschmann | 350/536 |
| 3,720,470 | 3/1973 | Berkhan | 350/536 |
| 4,003,707 | 1/1977 | Lübbers et al. | 436/172 |
| 4,339,241 | 7/1982 | Stöcker | 422/68 |
| 4,353,856 | 10/1982 | Mück et al. | 424/3 |
| 4,387,164 | 6/1983 | Hevey et al. | 436/166 X |
| 4,404,181 | 9/1983 | Mauthner | 424/3 |
| 4,435,508 | 3/1984 | Gabridge | 435/284 |

FOREIGN PATENT DOCUMENTS 1133598  3/1961  Fed. Rep. of Germany .......... 424/3

OTHER PUBLICATIONS

Ames Division, Miles Laboratories; N-Multistix Reagent Strips (product publication) 1981.
Kawahara et al; Bonding Compositions to the Hard Tissue of Human Body; Chem. Abst. CA 94:197574, 1981.
Reusable Glass-Bound pH Indicators, Harper, Anal. Chem. V 47, No. 2, pp. 348–351.
Histopathologic Technique and Practical Histochemistry Lillie, 1965, p. 98.
Chemical Abstract (CA) 67(13): 1795h, Boyer, 1967.
CA 98(19): 157312Z, Huang et al, 1983.
CA 98(18): 148461V, Svoboda et al, 1982.
Aloe Scientific Catalog No. 103, 1952, p. 650.
The Section Freeze-Substitution Technique: I. Method, Chang et al, J. Histochem. & Cytochem. vol. 9, 1961.

*Primary Examiner*—Barry S. Richman
*Assistant Examiner*—Michael S. Gzybowski
*Attorney, Agent, or Firm*—Nixon & Vanderhye

[57] ABSTRACT

Processes for testing immobilized biological material with generally biochemical and histochemical methods, particularly enzyme, immuno and hormone chemical methods can be improved by adhering the biological material to the surface of a support and then fixing the support to a plate. The plate is constructed in such a way that the biological material is protected from damage. Using a biological testing technique such as thin section immunofluorescence testing the invention makes it possible to carry out biochemical tests in a more rational and trouble-free manner than with hitherto known methods. If necessary, a random number of tests can be performed side-by-side on a single plate. The invention makes it possible to simply and rapidly prepare frozen section products and store them in a space-saving manner at very low temperatures. The adhesion of the frozen sections to the support can be improved by coupling chemicals which react with the tissue by bonding thereto to the support.

13 Claims, 33 Drawing Figures

FIG.1A  Object (frozen section with antigens)

FIG.1B  Incubation: with antibody-containing serum

FIG.1C  Washing

FIG.1D  Incubation: with fluorescence-labelled antihuman serum

FIG.1E  Washing

PROCESS FOR ANALYSES TO BE CARRIED OUT ON IMMOBILIZED BIOLOGICAL TISSUE

FIELD OF THE INVENTION

The present invention describes an advantageous process and equipment for testing biological material which has been immobilized and for analyzing samples employing immobilized biological material.

BACKGROUND

The prior art and effectiveness of the present invention will both be illustrated using, as an example, the immunofluorescence testing of frozen sections.

In many patients, indirect immunofluorescence testing of frozen sections makes it possible to detect antibodies against the body's own tissue. The method was introduced by Coons et al (Coons A. H., Creech H. J., Jones R.N., Proc.Soc.Exp. Biol. N.Y., 47, 1941, p. 200ff).

Figure 1A:
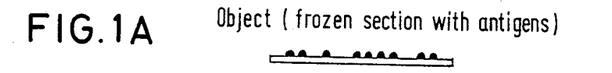
FIGS. 1A to 1E are diagrammatic illustrations of the indirect immunofluorescence test.
Figure 1B:
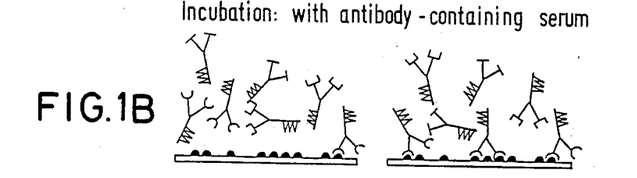
Figure 1C:
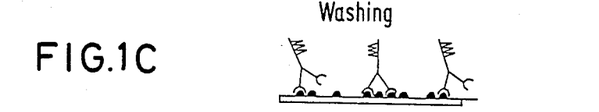

The method, with reference to FIG. 1, may be explained as follows. In a first stage, a frozen section of healthy tissue is placed on a glass surface and is allowed to thaw and dry. As illustrated in FIGS. 1A–1C, it is covered with the dilute serum of a patient. If the serum contains antibodies against the antigens of the tissue, they remain attached to the frozen section. Antibodies which are not directed against antigens of the frozen section do not become attached and are washed off.

Figure 1D:
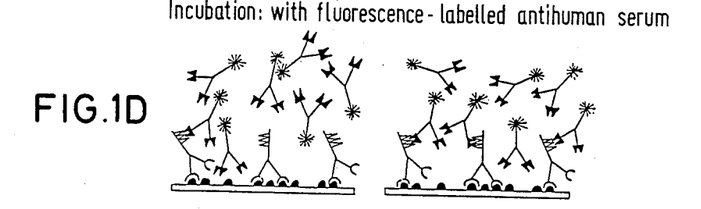
Figure 1E:
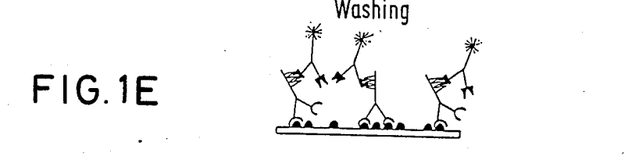

In a second stage, as illustrated in FIGS. 1D and 1E, antibodies obtained from animals and labelled with a fluorescent substance are then applied to the frozen section, these second stage antibodies being directed against the (already-attached) human antibodies (fluorescentlabelled antihuman serum). The (second stage) antibodies become attached to the (first stage) antihuman antibodies fixed to the frozen section and cannot be washed off.

Accordingly, if the patient's own serum contains antibodies against the tested tissue, the fluorescence microscope is able to detect the fluorescent label bonded to the corresponding tissue structures.

Frequently, direct frozen section immunofluorescence is used to investigate the tissue of patients in order to establish whether antibodies have become attached to certain tissue structures in vivo. For this purpose, frozen sections of the tissue are made and, in a direct immunofluorescence test, are brought directly together with a fluorescence-labelled antihuman serum, the first stage of the aforementioned indirect immunofluorescence test being omitted. The antibody-containing structures fluoresce in the washed products.

Different frozen section immunofluorescence techniques for physically manipulating frozen sections are known to those skilled in the art, but each has disadvantages. The techniques and their attendant disadvantages will be reviewed as part of the background discussion which follows.

It is standard practice when using immunofluorescence tests to mount the frozen sections on standard glass slides, a single slide generally being used for each frozen section. A detailed description of the test appears e.g. in Storch (Storch, W: "Immunfluoreszenzfibel", Fischer-Verlag, Jena, 1979). However, a number of sources of error are inherent in the test, which consequently requires considerable skill and large expenditures on labor and material.

A first source of error often occurs if the drops of sera added to the frozen sections run and the frozen sections then dry out. If the frozen sections become dry during the test, the results can generally not be utilized. Thus, as a precaution, large drops are prepared and reagents are wasted.

A second source of error can occur when preparing the section for microscopy. Before carrying out microscopy, the frozen section is covered with glycerin containing phosphate buffered saline and a cover slide is placed over it and should float on the glycerin. If there is an excessive dropwise addition of glycerin, however, the cover slide generally slips with the result that the microscope is contaminated and excess glycerin must be wiped away. However, removing glycerin may exacerbate the situation if too much glycerin is removed so that, as a result of capillary forces, the cover slide is drawn firmly onto the slide and squeezes the frozen section. If the cover slide is accidentally moved very tightly against the standard slide, the frozen section will likely be destroyed.

The same type of error may occur if, during microscopy, the frozen section is to be brought into the focal plane of the objective and the cover slide is brought too close to the objective. As a result, a positive result can appear negative.

Sera from different patients can be simultaneously tested on one slide. This allows combining operating sequences so that the testing process is simplified. Several frozen sections must be placed side-by-side on the slide beforehand and it must be ensured that there is no intermixing between the sera. Such simultaneous testing is facilitated by subdividing the slide into "reaction fields" which are set off from one another by a water-repelling coating on the slide (O'Neill, P., Johnson, G.D; Ann. N.Y. Acad. Sci. 177, 446–452, 1971; U.S. Pat. No. 3,736,042; EP-OS No. 79 103 987.8) or by color rings (Räisänen, S et al, J. Clin. Pathol. 33, 95–96, 1980). The more sera that are to be investigated on a slide, the smaller the preparatory expenditure during each individual test.

However, the aforementioned "simultaneous" testing technique is not conductive to carrying out more than about 20 individual tests on the same slide, particularly because the reaction fields are subject to successive dropwise application (of sera), resulting in different incubation times for the individual analyses. Testing more than about 20 samples thus generally produces too much variation in incubation time between the first and last sections. Additionally some sections might dry out and become unusuable during the period of time fluorescence-labelled antihuman serum is being added dropwise to other sections.

When large numbers of sera have to be tested side by side, e.g. 96 sera on one slide (see FIG. 2), the methods according to Stöcker are available (EP-OS No. 79 103 987.8; DE-OS No. 3,107,964). Hydrophilic reaction fields are present in a congruent arrangement on two plates and are surrounded by a water-repelling coating. Frozen sections are placed on the reaction fields of one plate, while samples, e.g. serum dilutions or the fluorescence-labelled antihuman serum are added dropwise to the reaction fields of the other plate. Both plates are then placed in a frame in such a way that the frozen sections are immersed in the liquid samples. All the frozen sections of one plate are incubated for the same period of time and no frozen section dries out during the test, even during the application of the fluorescence-labelled antihuman serum.

The above method for testing large numbers of sera on one plate has hitherto been adopted in immunofluorescence diagnosis only in cases where it is possible to use suspendable antigens, because they can be added dropwise to the reaction fields, e.g. toxoplasmosis or loose exciters. However, those skilled in the technology of making frozen sections appreciate how difficult it can be using hitherto known processes to place 96 frozen sections cleanly and uniformly on the reaction fields of a plate. There is a high level of waste in industrial production.

It is often necessary to seek antibodies against various antigens in a serum. Several suspendable antigens can be added dropwise side by side on a reaction field and, after drying and optionally fixing, they are jointly covered with one serum dilution drop (Wang, S.P., Excerpta Medica, Amsterdam, 273-288, 1971). If one wishes to verify antibodies against different tissues, several frozen sections may be formed into a "composite section", which is then covered with a large sample or reagent drop. For this purpose, the frozen sections for each tissue can be individually produced and different frozen sections can be juxtaposed on one reaction field.

Alternatively, several fragments of different tissues can be jointly frozen into an aqueous solution of carboxymethylcellulose, followed by the simultaneous sectioning and mounting thereof (e.g. Nairn, R.C.: "Fluorescent Protein Tracing", Churchill Livingstone Edinburgh, 1976). Only a few organ fragments can be cut together in a block, however, and the fragments must be accurately trimmed to size. Moreover, this technique requires a great deal of skill and tissue may be lost. Also, frozen sections to be fixed in different ways cannot be juxtaposed in the same "composite section".

On one hand it is frequently the case that there is only little fluorescence-labelled antihuman serum or serum to be tested available for use. The test batch must then be kept as small as possible, the prerequisite for this being small frozen sections. The tissue is cut to the desired size and account is taken of the amount of material lost.

On the other hand, in the case of testing structures distributed in a non-uniform manner in the tissue, e.g. Langerhans islands of the pancreas or glomeruli of the kidneys, large sections are required in order to be sure that the desired structures are present during microscopy. It is otherwise extremely difficult (and perhaps prohibitively so) to cut islands or glomeruli from the loose frozen section.

It is frequently the case that the available organ fragments are so small that only very few frozen sections can be obtained therefrom, and the number of sections is not sufficient for the various tests to be performed. However, the structures which are of interest are frequently represented many times on these sections. An attempt can accordingly be made to subdivide the finished loose sections, either fresh or after freeze-drying. However, the desired structures are difficult to detect on the loose section and the manipulations involved in subdividing are generally very difficult.

A particular difficulty in biochemical tests on frozen sections is that the sections frequently adhere poorly to the substrate during incubation and often partly or wholly float off. If glass slides are used as the substrate, they must consequently be very carefully cleaned prior to the application of the frozen sections (chromosulphuric acid, ethanol, acetone; Storch W., see above). In certain laboratories, the glass surface is coated with glycerin and gelatin or with chicken protein (Romeis, B: "Mikroskopische Technik", Oldenbourg-Verlag, Munich, Vienna, 1968). This process constitutes no significant improvement, however, and is ignored by many scientists. For certain tissues, such as lungs, intestinal mucosa and particularly fat-rich tissue (e.g. pancreas, adrenal medulla), there has hitherto been no reliable process for maintaining unfixed frozen sections firmly on their substrate, particularly when long incubations are employed as part of the test procedure and where thorough washing must take place.

Consequently, it is therefore conventional practice to use unfixed tissue in immunohistochemistry (Wick, G. et al: "Immunofluorescence", Medizinische Verlagsgesellschaft Marburg/Lahn, 1978). Only if the antigen is soluble in water is the frozen section fixed, e.g. as in the case of the thyroid gland which has a colloid that may be made insoluble by treatment with absolute methanol.

Numerous processes are known enabling organic material to be bonded to activated surfaces. Particular efforts are being made to immobilize enzymes, antigens and antibodies on solids (e.g. Ternynck, T., Avrameas, S., FEBS-Letters 23, 24–28, 1972; Guesdon, J. L. et al, J. Immunol. Meth. 21,59–63, 1978; DE-AS No. 2,102,514; DE-OS No. 2,740,008; DE-OS No. 2,749,317; German Pat. No. 2,905,657). A description has already been given of cutting tissue embedded in polyacrylamide and bonding the sections chemically on a surface provided with reactive groups (Hausen, P., Dreyer, C., Stain Technol, 56, 287–293, 1981). It is therein assumed that it is the polyacrylamide which binds to the surface, not the tissue. However, the fact that a frozen section can firmly join itself (as unembedded tissue) to a surface which has been activated by being chemically treated so that it contains reactive groups, which section would not otherwise adequately adhere to an untreated surface, was clearly not recognized by these authors, and the technical literature otherwise fails to report thereon.

SUMMARY OF THE INVENTION

The purpose of the invention is to provide an improved process enabling tests to be carried out on immobilized biological material, together with equipment for performing the same.

As a result of the invention, it is possible to immobilize biological material by chemically bonding it to a surface and to then rationally test it with biochemical methods or use it for rational biochemical tests. The description which follows employs immunofluorescence on frozen sections of biological tissue for purposes of illustration only. Those skilled in the art will appreciate that the invention is also suitable for numerous other applications in other fields of immunology (such as fluorescence immunoassays, radio immunoassays, enzyme immunoassays), histochemistry, microbiology, clinical chemistry and hormone chemistry.

DETAILED DISCUSSION

In the specification and claims the term "plate" is used to designate a planar substrate or support into which reaction fields, as depressions, wells, etc. are cut or otherwise placed for the purpose of receiving supports having biological material immobilized thereon. The depressions can have various geometries (circular, square, elongated, etc.) and their depth is measured from the top surface of the plate. The particular spot in the depression to which the support is fixed is a "reaction field" (as previously explained), and is the position at which serum is contacted with the frozen section or other biological material. The term "support", like the term "plate", designates a planar substrate or support. The support has much smaller dimensions than the plate, however, dimensions small enough to allow the support to fit comfortably within the "depressions" or reaction fields in the plate. Importantly, the thickness dimension of the support is such that, when combined with a section of biological material immobilized on its surface, the thickness of the support plus biological material will be equal to or less than the depth of the depression. A planar protective sheet or surface designated herein as a "cover slide" or other "facing surface" may then be placed, supported by the top surface of said plate, over the depression to protect the immobilized biological material, but with the cover slide itself at most just touching the biological material or section.

Generally the invention provides a process for carying out tests on immovable biological material with general biochemical and histochemical methods, particularly the methods of enzyme, immuno and hormone chemistry, in which one or more tests are carried out side by side on a plate and in which the biological material is largely protected against damage, wherein the biological material is initially made to adhere to the surface of one or more supports and then the supports or parts thereof are fixed to a plate together with the biological material, the surface carrying the biological material being arranged in such a way that it has no direct contact with solid objects and when this is undesired, does not dry during testing.

More specifically, the invention provides a process for protecting biological test material, comprising the steps of:

immobilizing said biological material by adhering it to the surface of at least one support; and fixing said at least one support within at least one depression in a plate, said at least one depression having a depth equal to or greater than the combined thickness of said support and said biological material.

Following fixing the support plus biological test material (i.e. on a reaction field), a cover slide or other facing surface may be placed over the depression as protection. The facing surface, at most, lies adjacent the biological material without squeezing it. Advantageously there is a definite finite distance $\Delta h > 0$ between the biological test material and the facing surface.

The biological material is firstly placed on a support to which it is allowed to adhere. One or more supports or parts 1a thereof are then adhered to a plate 2 or fixed thereto with other means. Using flat plates, unless other precautions are taken, the biological material is particularly sensitive to damage or drying out because it is raised above the level of the flat plate by the support and the adhering biological material. Thus, it is not possible to carry out immunofluorescence tests by conventional methods in this manner. The cover slide which is ultimately applied rests directly on the exposed sensitive frozen sections and squeezes them.

Figure 4A:
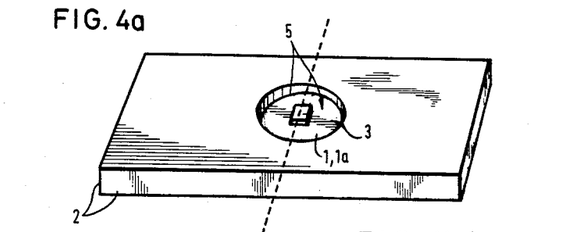
FIG. 4 schematically illustrates a plate 2 with a support 1a fixed thereto in perspective plan view (a), cross-section (b) and with a cover slide in cross-section (c).
Figure 4B:
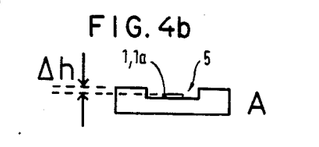
Figure 4C:
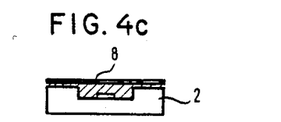
Figure 6A:
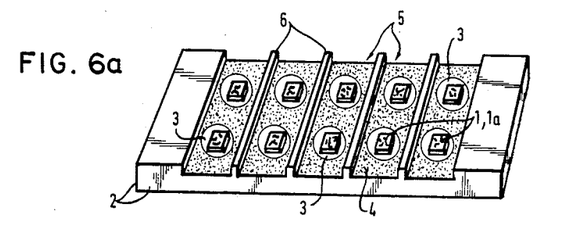
FIG. 6 is a perspective view illustrating a plate 2 (a) having supports 1a fixed thereto and an associated reagent support 7 (b) with hydrophilic reaction fields 3 and hydrophobic surrounding area 4.
Figure 6B:
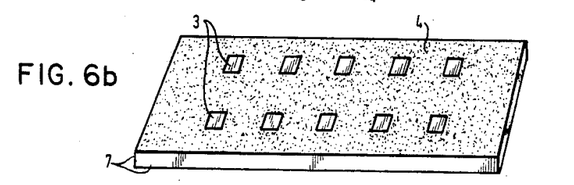

However, in the present invention the slides are placed on the plate in such a way that the biological material is largely protected against damage, and particularly during the actual testing, such that it is not squeezed between the plate and cover slide. It is also ensured that, after the test, the frozen section does not dry out if such is undesired. According to the invention, for this purpose the supports are each fixed in depressions 5 of plate 2 as shown in FIGS. 4 and 6. The depth of depression 5 relative to the thickness of support 1a is such that a reliable finite distance $\Delta h \geq 0$ exists between the biological material and the top surface of plate 2.

Instead of housing support 1a within depression 5, it is also possible to use other geometrical or mechanical means and embodiments, as shown in FIG. 13, to set a spacing $\Delta h \geq 0$ between the biological material and a facing surface such as cover slide 8. If the biological material is to be assessed with the microscope or some other aid, this distance $\Delta h$ must be fixed in such a way that the biological material can be placed in the focal plane of the objective, or in a plane which can be reached by the sensor of the particular aid used.

Figure 5:
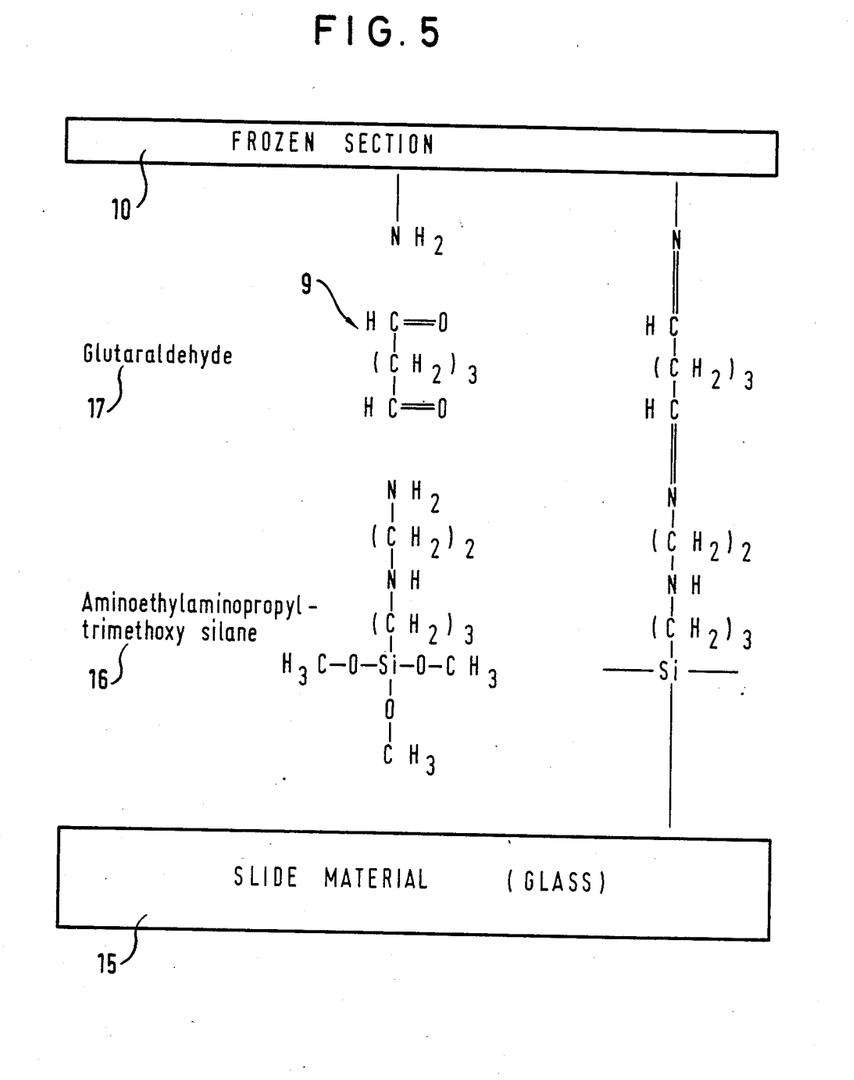
FIG. 5 is a diagrammatic view which illustrates how a frozen section can be chemically coupled to a support.

According to the invention, frozen sections can be chemically bonded to the support, in such a way that reactive chemical groups (9, see FIG. 5) are coupled to the support surface prior to the application of the frozen sections, as shown in FIG. 5. However, it is also possible to use the invention with conventionally produced frozen sections, i.e. which are not chemically bonded to the slides.

The invention has numerous advantages.

As a result of the arrangement protecting the biological material, the test results are also protected. The results are more reproducible and the percentage of unsuccessful tests can be reduced from 5–10% virtually to zero. During transportation and testing, the frozen sections are not nearly as easily damaged as when using conventional flat plates. Frozen sections can be covered with glycerin by untrained personnel, and they are not destroyed by the cover slide, even if the latter presses firmly on the plate.

In FIG. 4 the reaction field 3 is in a plane lower (by virtue of being the bottom surface in depression 5) than the area directly adjacent to the reaction field, such that the surface of a support 1a does not project over the plane of the surrounding area. This prevents running of the serum dilution, the fluorescence-labelled antihuman serum or the glycerin and, consequently, there is no drying out of the frozen sections.

Histological products such as thin sections of biological tissue, particularly frozen sections, or products formed from other biological materials bonded to surfaces can be produced relatively cheaply, in large number, and in high quality.

It is sometimes better not to apply the biological material directly to a plate, but instead to coat a support with it and then, in an independent second stage, to fix it with the support to a plate (plate in histochemical tests=slide). To produce supports for non-histochemical tests it is possible to coat e.g. 10,000 glass fragments (3×3×0.2 mm) in a small 250 ml volume vessel. The glass fragments can then be rapidly and simply adhered to a plate, e.g. by an automatic machine. Alternatively, the biological material may be spread onto a slide and allowed sufficient time to adhere thereto. The slide may then be comminuted into fragments and the fragments adhered to a plate.

The coated slides take up little space and are not destroyed at low temperatures. Thus, they are better suited to preservation under deep-freezing conditions than e.g. standard glass slides. Frozen section fragments may be preserved (approximately 2×2×0.2 mm—as supports, e.g. cover slide material can be used) in PVC hoses or in glass ampoules which may then be sealed and stored for many years in liquid nitrogen at −196° C., e.g. 1000 pieces in a 1 ml glass ampoule.

Figure 3:
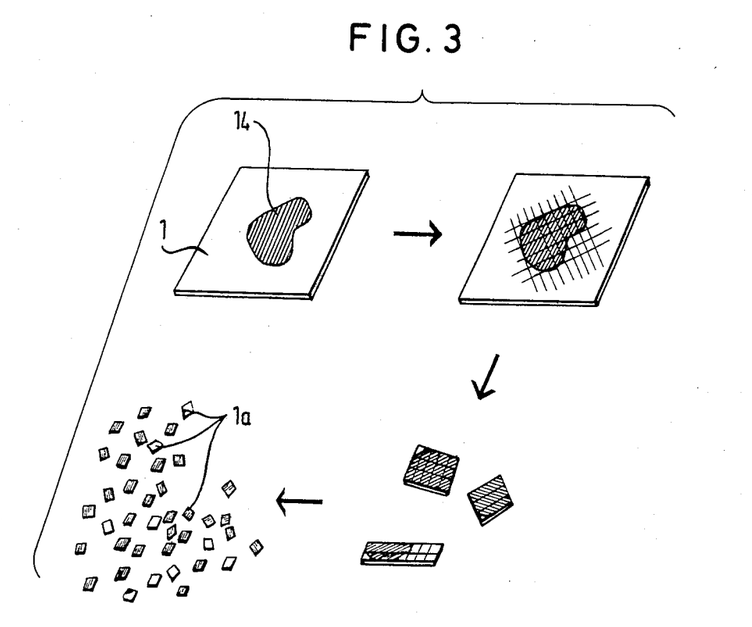
FIG. 3 is a schematic illustration of the rational production of a plurality of frozen section fragments 1a from frozen section 14 with the aid of a dividable support 1.

According to the invention, frozen sections can be easily fragmented by adhering to a support which is itself easily dividable. It normally requires considerable skill to cut an interesting or desired area of appropriate size from an individual loose frozen section. If the frozen section is stabilized by a slide, however, isolation of one or more desired areas can be carried out very easily. This technique of dividing e.g. a cover slide into fragments is illustrated in FIG. 3.

For microanalyses, 100 miniature frozen sections can be cut from a 5×5 mm frozen section adhering to a cover slide within 5 minutes.

Frozen sections of individual glomeruli can easily be separated from a frozen kidney section adhering to a cover slide. The tissue is better utilized because there is no need to use far more glomeruli than necessary for each individual test. No reagents are wasted for those parts of the frozen sections which contain no glomeruli. Thus, the invention is particularly suitable for tests in which the reagents are very expensive, as in the case of monoclonal antibodies, or in which little test material is available, as is normally the case when plasmacytoma cells have to be identified.

Figure 2:
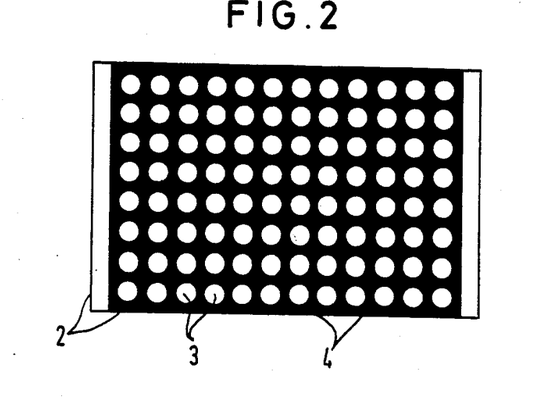
FIG. 2 is a schematic illustration of a flat plate having 96 hydrophilic reaction fields 3, their surrounding area 4 being hydrophobically coated.
Figures 8A, 8B:
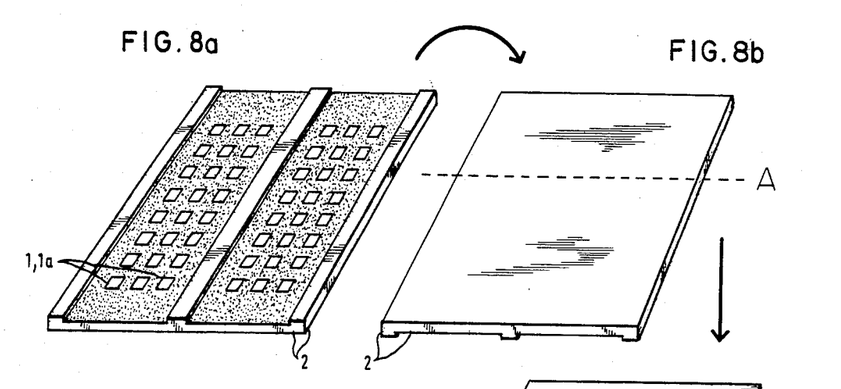
FIG. 8 is a perspective view illustrating a plate 2 (a) with 48 supports 1a fixed thereto; the back surface (b) of said plate, and the associated reagent supports 7 (c) and both during incubation in cross-section (d).
Figure 8C:
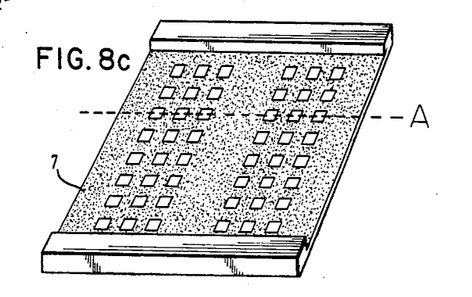
Figure 8D:
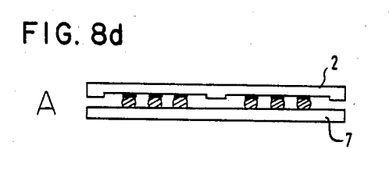
Figure 9A:
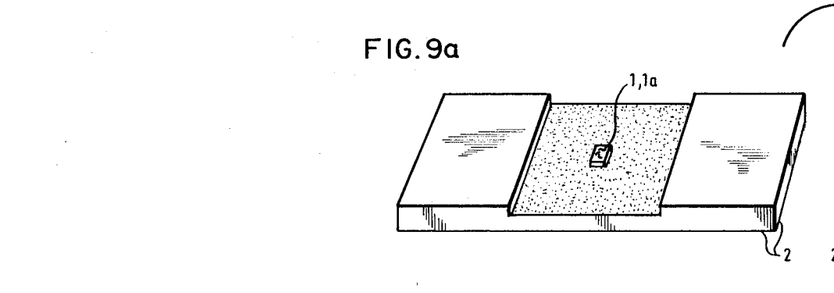
FIG. 9 shows a plate 2 (a) with one support 1a fixed thereto; the back surface (b) of said plate, the associated reagent support 7 (c) and both of them during incubation in cross-section (d).
Figure 9B:
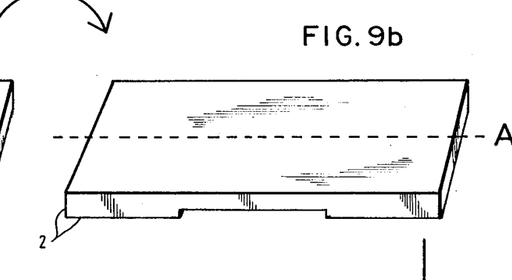
Figure 9C:
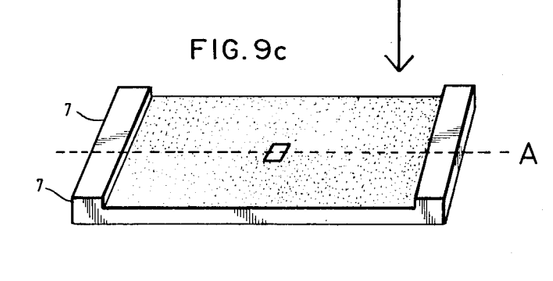
Figure 9D:
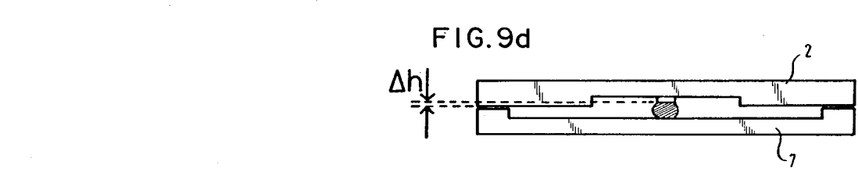

Unlike processes presently known to the art, the invention makes it possible to fix numerous frozen sections to a plate with numerous reaction fields, as illustrated in FIGS. 2 and 8. The inventor employs tests plates having 96 reaction fields, each reaction field having a frozen section thereon.

It is equally easy to produce "composite sections". The composition of the "diversified sections" can be varied at random between individual tests. It is possible simultaneously to test, side-by-side, tissue sections which have been pretreated in different ways, e.g. fixed and unfixed frozen sections of the thyroid gland. The frozen sections are fixed to the support before the latter is fragmented and adhered to the plate. It is therefore also possible to use fixing processes which attack the hydrophobic coating of the plate.

As a result of chemically activating the support surface, the frozen sections adhere surprisingly well and, during incubation or washing processes, there is no longer a risk of washing them away, not even if they are kept for several days in the liquid or if they are vigorously washed for a long time. Freeze-dried loose sections also bond to the activated slide in an aqueous medium. It was necessary for miniature analyses according to the invention to improve the adhesion of the frozen sections, because the latter frequently became detached from smaller slide fragments.

The following examples illustrate and explain the operation of the invention.

Example 1: Production of Activated Glass Supports

Example 1A (see FIG. 5): An adequate number of 0.2 mm thick cover slides were cleaned for 3 days in chromosulphuric acid and then adequately rinsed with distilled water. The cover slides were then immersed at ambient temperature in a 2% aminoethylaminopropyltrimethoxy silane solution in ethanol/water 1/1 (vol), washed 3 times for 1 minute in absolute ethanol and dried with compressed air. Cross-polymerization was allowed to take place overnight at 70° C., followed by a 3 hour immersion at ambient temperature in a 5% aqueous solution of freshly filtered glutaraldehyde. The slides were then adequately rinsed in distilled water and dried. By virtue of this treatment the surface of the cover slides now carried self-reacting aldehyde groups 9 which could covalently bond via free amino groups to proteins in the frozen sections. The cover slides were stored for 6 months at ambient temperature without any significant activity loss.

Example 1B: Cover slides were cleaned as in Example 1A and then immersed for 3 hours at ambient temperature in a 2% methacryloxypropyltrimethoxy silane solution in ethanol/water 1/1 (vol), dried with compressed air, kept at 70° C. for 2 hours, immersed for 12 hours in 5% acrolein, washed 3 times for 15 minutes in distilled water and dried with compressed air. The surface of the cover slides now carried self-reacting aldehyde groups. The cover slides were stored for up to 6 months before they were coated with the frozen tissue sections.

Example 1C: Cleaned cover slides were immersed for 3 hours at ambient temperature in a 2% mercaptopropyltrimethoxy silane solution in 1% acetic acid in ethanol/water 1/3 (vol), and dried with compressed air. Their surface carried now self-reacting mercaptogroups, that were able to bond mercaptogroup-bearing frozen tissue sections under oxidizing conditions.

Example 1D: Cleaned cover slides were immersed for four hours at ambient temperature in a 0.1% solution of polylysine (400 000 daltons), washed 3 times in distilled water and dried with compressed air. The surface of the cover slides now carried aminogroups which could react with components of the frozen sections via ionic bonds. The cover slides were now ready to be coated with the frozen tissue sections or to be further processed as described in Example 1E.

Example 1E: Cover slides activated according to Example 1D were immersed for 3 hours at ambient temperature in a 5% aqueous solution of freshly filtered glutaraldehyde. The slides were then rinsed in distilled water and dried. Their surface now carried aminogroups with a capacity to attach frozen tissue sections via ionic bonds, as well as self-reacting aldehyde groups.

Example 2 (FIG. 3): Production of Frozen Section Fragments

Freshly prepared 5 μm thick frozen sections 14 of human liver were placed on cover slide 1 produced according to example 1, such that almost the entire surface of one side of cover slide 1 was coated. The frozen sections were allowed to thaw and dry. A diamond tip was used to scratch fields into the cover slide in the area coated with the frozen sections, followed by subdividing the cover slide into fragments. Part of the frozen section fragments 1a were set aside for example 3, the remainder being placed in polyvinyl chloride hoses which were sealed and stored in liquid nitrogen.

It is easier and several times faster to produce 50 fragments as described above by fragmenting a large frozen section on a glass slide (time taken a quarter minute) and then to adhere the glass-supported fragments to a plate (5 minutes) than to cut 50 frozen sections from a small tissue portion using a cryotome, followed by placing the sections on a standard slide (30 minutes). There is also a better utilization of the tissue, because the material lost when preparing a small tissue portion is retained.

Using the invention, specifically the "fragmented support" technique described above, it is possible to seek out interesting tissue areas using a magnifier microscope, while discarding unimportant areas and areas with a poor cut quality.

The cover slide can be scratched or scored for breakage into fragments prior to applying the frozen section thereon. A frozen section can also be placed on closely juxtaposed glass fragments, followed by thawing and drying and the subsequent application of the fragments to a plate. The slide can also be made from plastics, e.g. foils made from polymethylmethacrylate with reactive groups. It is possible to punch or cut fragments from the foils, e.g. using a laser.

Example 3 (See FIGS. 6 and 7): Performing an Immunofluorescence Test

In the following test, the sera of patients were tested for antibodies against nuclei. For this purpose, and referring to FIG. 6 the frozen section fragments 1a produced in example 2 were stuck to reaction fields 3a of a plate 2. The frozen sections were at a level which was 0.1 mm lower than the top surface of ribs 6 present on plate 2. The thickness of the ribs was about 0.3 mm.

Figure 7:
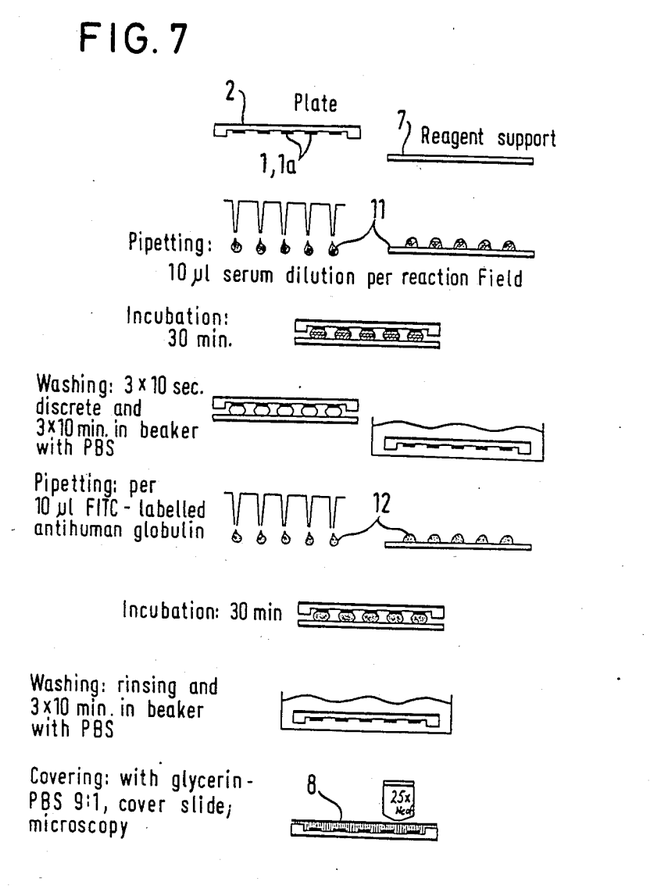
FIG. 7 is a diagrammatic illustration of an indirect immunofluorescence test according to the invention.

Referring to FIG. 7, drops 11 of diluted sera were applied to reagent support 7. The frozen sections adhering to supports 1a were then immersed in the drops for 30 minutes at ambient temperature and then washed in phosphate-buffered saline PBS, firstly discretely with the aid of a second reagent support 7, then in a beaker. This was followed for 30 minutes by a second incubation of the frozen sections with fluorescence-labelled antihuman serum 12. After a further incubation and washing process, glycerin containing phosphate buffered saline was applied and a cover slide placed over it. The frozen sections were observed with the fluorescence microscope. The same results as with the conventional method were obtained when determining the antibodies against nuclei in 200 different sera. The work expended with the new method was 10 times less and the reagent consumption 3 times less than with the conventional method.

The same operations can be carried out using plates having a random number of reaction fields, e.g. with 1 as illustrated in FIG. 9 or with 48 as illustrated in FIG. 8.

Figure 10:
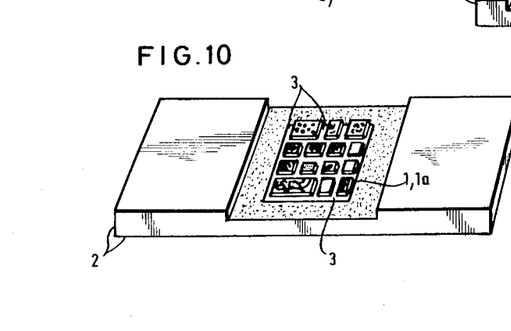
FIG. 10 is a perspective view illustrating a plate 2 with a plurality of supports 1a having different frozen sections on a reaction field 3 ("composite section").
Figure 11A:
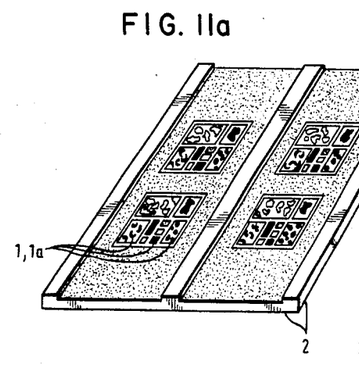
FIG. 11 is a perspective view illustrating a plate 2 (a) with four "composite sections", their back surface (b) of said plate, the associated reagent support 7 (c) and both of them during incubation in cross-section (d).
Figure 11B:
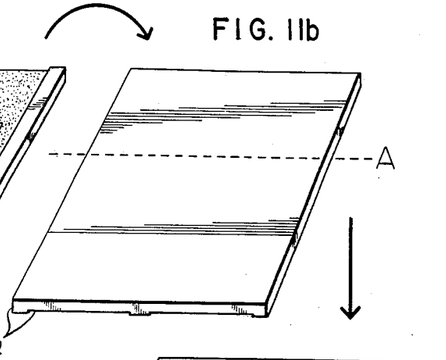
Figure 11C:
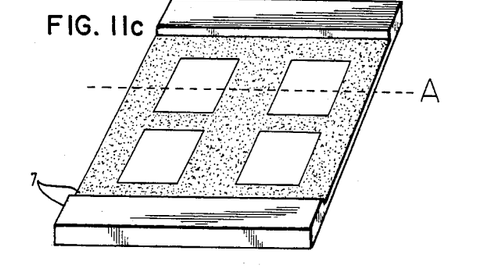
Figure 11D:
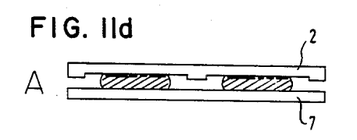

Several supports with frozen sections of different tissues can be adhered to each reaction field ("composite section", illustrated in FIGS. 10, 11 and 14)—one reaction field per plate (FIGS. 10 and 14) or several reaction fields per plate (FIG. 11).

Figure 12:
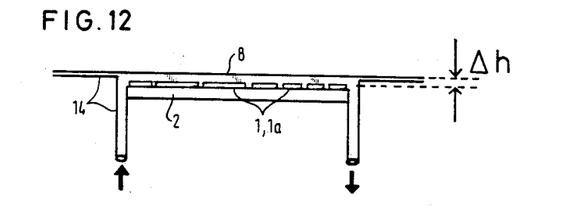
FIG. 12 is a sectional view illustrating a flow cell, whose base is formed by a plate 2 and to which are fixed several supports 1a with frozen sections (also a "composite section").

Supports having frozen sections can also be adhered to the bottom of a flow cell 14, as illustrated in FIG. 12, the top of said cell being constituted by cover slide 8 positioned a safe distance Δh>0 above the frozen sections 1a, but still permitting observation with the microscope. For incubation purposes, the flow cell is simply filled with the serum dilution or with the fluorescence-labelled antihuman serum. The pH-buffered common salt solution is continuously pumped through for washing purposes. This closed arrangement has the advantage that during the test the frozen sections do not dry out as easily and there is less danger to laboratory personnel as a result of infectious sera.

Figure 13A:
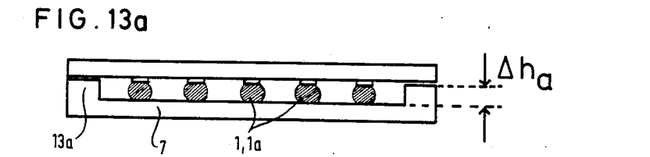
FIG. 13 is a sectional view illustrating a plate 2 with 5 supports 1a fixed thereto and the associated reagent supports 7 during incubation, in cross-section (a), the same plate with cover slide 8 (b).
Figure 13B:
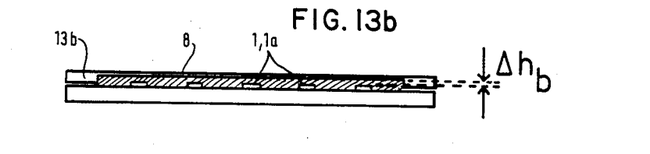
Figure 14A:
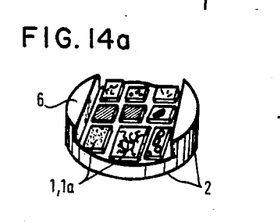
FIG. 14 illustrates a disk-shaped "plate" 2(a), its back surface with knob (b), the associated reagent supports 7 (c), during an incubation in cross-section (d) and the plate covered with glycerin and held by capillary force against a cover slide, under the microscope (e).
Figure 14B:
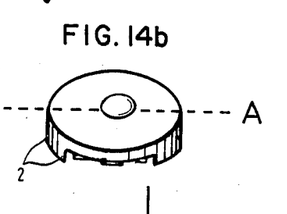
Figure 14C:
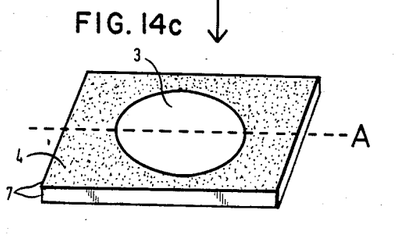
Figure 14D:
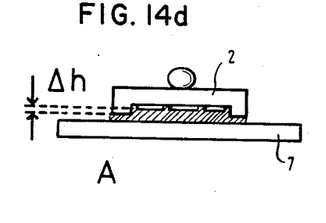
Figure 14E:
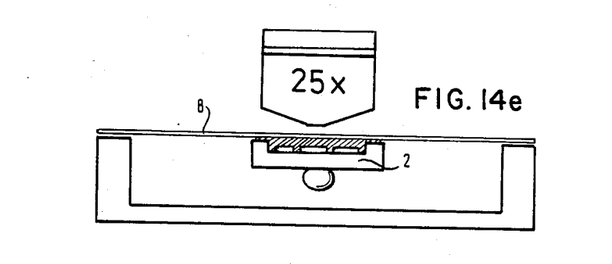

FIG. 13 shows that spacers (13a, 13b) can produce the distance Δh necessary for protecting the biological material on the surface of support 1a. Said spacers can be part of a reagent support 7 (FIG. 13A) or cover slide 8 (FIG. 13B) facing plate 2.

In FIG. 14, a disk-like "plate" 2 is shown onto which can be adhered frozen section fragments 1a. This plate is made from a 0.3 mm thick circular cover slide, onto which are stuck two 0.3 mm thick strips or ribs 6. During incubation, the "plate" floats on the serum dilution or on the fluorescence-labelled antihuman serum, which is added dropwise to reaction field 3 of reagent support 7. For microscopy glycerine containing phosphate buffered saline is introduced between the frozen sections and the cover support and the "plate" is secured by a capillary force to cover slide 8.

What is claimed is:

1. A process for preparing biological tissue, for storage and testing thereof comprising the steps of:
   (1) immobilizing a biological tissue by adhering it to a surface of at least one dividable support having at least two surfaces;
   (2) breaking or cutting said dividable support into at least one smaller support; and
   (3) fixing said at least one smaller support with the immobilized biological tissue thereon onto a plate.

2. The process of claim 1 wherein said plate has at least one depression therein and said immobilized biological tissue is fixed to reaction fields in said at least one depression.

3. The process of claim 1 wherein said biological tissue is a thin histological section.

4. The process of claim 1 wherein said at least one dividable support is a glass disc.

5. The process of claim 1 wherein said biological tissue comprises frozen sections which are adhered to the surface of said support by:
   coupling to said support a chemical substance having groups reactive with said frozen sections, and
   chemically reacting said frozen sections with said reactive groups, thereby covalently bonding said sections to said support.

6. A process for preparing biological tissue for storage and testing thereof comprising the steps of:
   (1) immobilizing a biological tissue by adhering it to a surface of at least one dividable support having at least two surfaces;
   (2) breaking or cutting said biological support into at least one smaller support; and
   (3) fixing said at least one smaller support with the immobilized biological tissue thereon within at least one depression in a plate, said at least one depression having a depth equal to or greater than the combined thickness or said support and said biological material.

7. The process of claim 6 wherein said at least one depression is covered with a cover slide which is supported by a surface of said plate.

8. The process of claim 6 wherein said at least one depression defines a base of a flow cell, said at least one support having biological tissue immobilized thereon being fixed to said base at a distance $\Delta h \geq 0$ from a top surface of said cell, and wherein reagent solutions used for testing said biological tissue are caused to flow through said cell.

9. The process of claim 6 wherein said biological tissue comprises frozen sections which are adhered to the surface of said support by:
   coupling to said support a chemical substance having groups reactive with said frozen sections, and
   chemically reacting said frozen sections with said reactive groups, thereby covalently bonding said sections to said support.

10. A process for adhering thin sections of frozen biological tissue to a support, comprising the steps of:
    coupling to a support a chemical substance having reactive groups which react with a frozen biological tissue; and
    chemically reacting said frozen biological tissue with said reactive groups and thereby covalently bonding said frozen biological tissue to said support.

11. The process of claim 10, wherein:
    said support is made of a material which reacts with silanes, and
    said chemical substance is a silane having at least one amino group which has been reacted with at least one compound having at least two aldehyde groups.

12. The process of claim 10, wherein:
    said support is made of a material which reacts with silanes, and
    said chemical substance is a silane having at least one methacryl group or acryl group which can be reacted with at least one compound having at least one group which reacts with methacryl groups or acryl groups and at least one aldehyde group.

13. The process of claim 10, wherein:
    said support is made of a material which reacts with silanes, and
    said chemical substance is a silane having at least one mercapto group.

* * * * *